United States Patent [19]

Kegel et al.

[11] Patent Number: 4,806,479
[45] Date of Patent: Feb. 21, 1989

[54] USE OF STABILIZING AGENTS IN CULTURE MEDIA FOR GROWING ACID PRODUCING BACTERIA

[75] Inventors: Mary A. Kegel, Sun Prairie; Donald L. Wallace, Madison, both of Wis.

[73] Assignee: Miles Inc., Elkhart, Ind.

[21] Appl. No.: 733,328

[22] Filed: May 13, 1985

[51] Int. Cl.$^4$ ............... C12N 1/38; C12N 1/20; A23C 9/123; A23C 19/032
[52] U.S. Cl. ............... 435/244; 435/252.1; 435/253.4; 426/38; 426/43
[58] Field of Search ............... 435/139, 244, 253, 243, 435/260, 853, 854, 855, 856; 426/41, 43, 38

[56] References Cited

U.S. PATENT DOCUMENTS

| | | | |
|---|---|---|---|
| 3,539,363 | 11/1970 | Morgan et al. | 426/43 |
| 4,282,255 | 8/1981 | Sandine et al. | 426/7 |
| 4,402,986 | 9/1983 | Sinkoff et al. | 426/41 |
| 4,416,905 | 11/1983 | Lundstedt et al. | 426/34 |

Primary Examiner—Elizabeth C. Weimar
Attorney, Agent, or Firm—Jerome L. Jeffers

[57] ABSTRACT

Disclosed is a bulk starter medium for the propagation of a mother culture of an acid producing bacteria which medium contains a carbohydrate source, a nitrogen containing growth stimulant, a phage control agent and an essentially insoluble or temporarily insolubilized neutralizing agent to which has been added a foodgrade hydrocolloid stabilizing agent.

13 Claims, No Drawings

USE OF STABILIZING AGENTS IN CULTURE MEDIA FOR GROWING ACID PRODUCING BACTERIA

BACKGROUND OF THE INVENTION

The present invention relates to bulk starter media for cheesemaking and, in particular, to a bulk starter media which contains particulate, insoluble materials as neutralizing agents. In the commercial production of cheese, large vats of milk are treated with a milk clotting agent such as rennin and inoculated with lactic acid producing bacteria such as *Streptococcus lactis, S. cremoris, S. thermophilus* and *Lactobacillus bulgaricus*. These lactic acid producing bacteria are capable of fermenting lactose or other similar carbohydrates to produce lactic acid.

The bacteria is generally propagated from a mother culture in large enough quantities of aqueous medium to produce a bulk starter which can then be used for fermenting the final batch of milk to produce cheese as the final product. In a typical procedure, a bulk starter medium is prepared by dissolving a dry powder comprising a nutrient base and a growth stimulant, together with alkali metal phosphate and/or polyphosphate phage control agents in water to a level of about 8% solids. The solution is sterilized and cooled whereupon it is inoculated with the lactic acid producing bacteria which is allowed to incubate. After incubation, the "ripened" starter is added to the cheese milk at a level of from about ½ to ¾ volume percent. The cheese milk at this point will have a pH of approximately 6.6, however, as the bacteria grows, the acid it produces will gradually lower the pH.

Neutralization is very important to the growth of the lactic acid producing bacteria because the acid produced impairs the growth of the bacteria and will eventually kill them, especially at a pH of 4.8 or below. Neutralization can be accomplished by the continuous addition of a water soluble base or an aqueous basic solution such as sodium hydroxide or ammonia gas so as to provide a pH which is maintained at 5.2 or above. Specialized equipment has been developed to monitor the pH of the growth medium and to add the neutralizing agent as needed. More recently, there has been disclosed in U.S. Pat. No. 4,282,255 the use of an essentially water insoluble or temporarily water insolubilized and thus initially solid form of a neutralizing agent. This patent mentions the use of magnesium phosphate and magnesium ammonium phosphate in particular. A magnesium ammonium phosphate neutralizing system in which magnesium ions, ammonium ions and phosphate ions are provided so as to form insoluble magnesium ammonium phosphate in situ is disclosed in U.S. Pat. No. 4,402,986.

While the employment of essentially insoluble or temporarily insolubilized neutralizing agents eliminates the need for the constant addition of base, their use presents another problem because of their insolubility. This is the case because the presence of the insoluble neutralizing agent requires agitation to keep it in suspension. This agitation adds cost to the process and is traditionally considered an undesirable procedure because culture growth may be detrimentally affected due to oxygen incorporation into the ripening starter. Accordingly, it would be desirable and it is an object of the present invention to provide a method for maintaining a particulate, insoluble material as neutralizing agent suspended in the ripening starter without the need for agitation.

SUMMARY OF THE INVENTION

The present invention is an improvement in the method of propagating a mother culture of an acid producing bacteria by inoculating an aqueous bulk starter medium containing a nutrient base, a growth stimulant, a phage control agent and an essentially insoluble or temporarily insolubilized, particulate material as neutralizing agent. The improvement comprises incorporating into the bulk starter medium a foodgrade protective hydrocolloid as stabilizer in sufficient amount to prevent settling out of the neutralizing agent from the medium.

DESCRIPTION OF THE INVENTION

The acid producing bacteria is normally propagated from a mother culture in large enough quantities of aqueous medium to produce a bulk starter which can then be used for fermenting the final batch of cheesemilk to produce the end product. A good starter must produce lactic acid in the cheese vat at a vigorous and steady rate as slow starters produce cheese of inferior quality. Some of the causes of starter slowness include infection by bacteriophage (phage), bacteria of low viability and a low bacterial cell population. The composition of the starter medium exerts a considerable influence on the loss of cell viability due to phage attack, and on maintenance of a desirable pH for the growth of acid producing bacteria.

A typical dry bulk starter medium may contain milk, whey and dextrose as nutrient base sources, an enzyme hydrolyzed casein and/or yeast as growth stimulant and mono-ammonium phosphate, di-ammonium phosphate and sodium hexametaphosphate or a combination thereof as the phage control agent. Suitable neutralizing agents include calcium carbonate, magnesium hydroxide, magnesium phosphate and magnesium ammonium phosphate. These inorganic salts are essentially insoluble in water which makes them desirable as neutralizing agents because they provide a buffering effect over a long period of time. Dissolving the dry bulk starter in water or milk at a level of about 8% (w/w) solids provides a suitable growth medium for the acid producing bacteria, but the insoluble nature of the particulate material, i.e. the neutralizing agent, necessitates constant agitation of the bulk starter medium to keep it in suspension. It has now been discovered that by adding a foodgrade protective hydrocolloid to the bulk starter medium before ripening, in an amount sufficient to prevent separation of the mixture, the necessity of constant agitation during the ripening process is eliminated.

In many food applications, stabilizers are used as thickening, suspending and emulsifying agents. All stabilizers increase the viscosity of the liquid medium and have the ability to bind or hold relatively large amounts of water. Exemplary of hydrocolloids useful as stabilizing agents are sodium carboxymethylcellulose, locust bean gum, sodium alginate, propylene glycol alginate, carrageenan and guar gum. Other suitable stabilizers include gelatin, gum exudates, karaya, tragacanth and gum arabic. It has been observed that care must be taken with the use of gelatin as stabilizer as it may thicken excessively and require agitation after ripening of the culture. Xanthan gum is preferred for use as the stabilizing agent because it is economical and effectively maintains the particulates in suspension.

In the practice of the present invention, the stabilizer is preferably mixed with the dry blended bulk starter media at the time of its preparation. Thus, the nutrient base, growth stimulant, phage control agent and neutralizing agent, which comprise the starter media, are mixed with the dry stabilizer and packaged as a single product. The addition of this material to an aqueous medium, usually with agitation, results in dissolution of the soluble ingredients. The neutralizing agent, which does not dissolve, is prevented from settling by the presence of the stabilizing agent, so that agitation, with its consequent disadvantages, can be terminated shortly after inoculation with the acid producing bacteria. Alternatively, the culture media can be put into water solution without the stabilizer and the stabilizer then added either as a dry material or a solution thereof. In either emodiment, the stabilizer is normally used initially in the form of a dry powder which assumes its functionality once it is rehydrated. The powder becomes uniformly distributed by the blending action required for preparation of the starter formulation.

A typical starter medium may contain milk and/or whey as the nutrient base source. Growth stimulants such as yeast extract and/or an enzyme hydrolyzed casein, are suitable growth promoters and the phage control agent can be of the citric acid type or, more commonly, an inorganic phosphate salt such as mono-ammonium phosphate, di-ammonium phosphate, sodium hexametaphosphate or a mixture thereof. The phage control agent of choice for the formulation described in U.S. Pat. No. 4,402,986 is an alkali metal tripolyphosphate. As mentioned above, it has been found desirable in certain instances to combine these ingredients with an essentially insoluble or temporarily insolubilized particulate material such as a neutralizing agent of the type described in U.S. Pat. No. 4,282,255. This is typically a base, a basic salt or a mixture thereof adapted to provide a controlled reaction with the acid produced by the bacteria without substantially raising the pH of the medium. This material is typically employed in a particulate form (preferably having a particle diameter of from 45 to 710 microns) and in an amount of from 0.5 to 8 weight percent of the combined dry weights of carbohydrate source, growth promoter and phage control agent.

The stabilizer prevents settling of the particulate material and thus eliminates the need for agitation which may interfere with the ripening of the media after it is inoculated with the acid producing bacteria. The stabilizer, as previously described, will be added to the dry blend bulk starter media or to its water solution in an amount sufficient to prevent settling of any insoluble, particulate material contained therein. This amount will vary depending on the amount and size of insoluble particulates involved, but will typically range from 2% to 6% of the dry bulk starter media on a weight basis.

The method of practicing the present invention is further illustrated by the following examples in which all percentages are on a weight/weight basis unless otherwise indicated.

EXAMPLE I

A dry bulk starter medium was prepared by combining the following ingredients with thorough mixing:

| Sweet Dry Whey | 41.2% |
|---|---|
| Magnesium Phosphate Tribasic | 17.6% |
| Ammonium Phosphate Dibasic | 17.6% |
| Tribasic Sodium Citrate Dihydrate | 17.6% |
| Yeast Extract | 6.0% |

To a portion of the above formulation was added Xanthan Gum to form Medium XG having a final composition as follows:

| Sweet Dry Whey | 38.45% |
|---|---|
| Magnesium Phosphate Tribasic | 16.43% |
| Ammonium Phosphate Dibasic | 16.43% |
| Tribasic Sodium Citrate Dihydrate | 16.43% |
| Yeast Extract | 5.60% |
| Xanthan Gum | 6.66% |

The medium without Xanthan Gum (designated Control) and Medium XG were rehydrated with water to 8.25% total solids, heated with agitation to 87.8° C. for 40 minutes and cooled to 22.8° C.

A one percent inoculation of both the Control and Medium XG was made with an active culture of WP *Streptococcus cremoris*. The inoculated media were incubated at 22.8° C. for 16 hours. An activity test was carried out by inoculating 0.5% (v/v) of the above 16 hours growth into steamed 11% (w/w) nonfat dry milk and incubating at 89° F. for 6 hours. The developed acidity was determined by subtracting the 0 hour value from the 6 hour value. Settling of particulates was observed at the times indicated in Table I.

TABLE I

| | WP Subculture acid prod'n | | | | Activity[a] test (Developed) acidity) | Cell Numbers (cfu/ml at 16 hours) | Settling[b] |
|---|---|---|---|---|---|---|---|
| | 0 hrs | | 16 hour | | | | |
| | TA[d] | pH | TA[d] | pH | | | |
| Control (8.25% w/w) w/agitation | 0.58 | 6.86 | 2.88 | 5.62 | 0.56 | $1.1 \times 10^9$ | − during incubation + during storage |
| Control (8.25% w/w) w/o agitation | 0.60 | 6.87 | 1.92 | 5.71 | 0.57 | $8.9 \times 10^8$ | + |
| Medium XG[c] (8.25% w/w) w/agitation | 0.60 | 6.82 | 2.88 | 5.57 | 0.57 | $1.0 \times 10^9$ | − (5 days) |
| Medium XG[c] (8.25% w/w) | 0.60 | 6.82 | 2.90 | 5.47 | 0.62 | $1.2 \times 10^9$ | − (5 days) |

TABLE I-continued

| | WP Subculture acid prod'n | | | | Activity[a] test | Cell Numbers | |
|---|---|---|---|---|---|---|---|
| | 0 hrs | | 16 hour | | (Developed) | (cfu/ml at | |
| | TA[d] | pH | TA[d] | pH | acidity) | 16 hours) | Settling[b] |
| w/o agitation | | | | | | | |

[a] 6 hr-30° C. activity test in 11% nonfat dry milk with TA readings at 0 hrs and 6 hrs (developed acidity is the change in TA readings at 0 and 6 hrs) - inoculation rate was 0.5%.
[b] Settling: − = no settling in the indicated time + = severe settling
[c] XG = Xanthan Gum
[d] TA = Titratable acidity as lactic acid From Table I it can be determined that culture growth and performance in Meiium XG without agitation were equal to or greater than the Control with agitation and Medium XG with agitation. The Control without agitation shows the expected reduced subculture growth and cell numbers caused by settling of the particulates. Culture growth indicates that the stabilized medium is not detrimental to growth and that incubation without agitation yields a very active culture.

EXAMPLE II

Certain lactic acid producing bacteria are more sensitive to the presence of oxygen than others. Those culture strains which are the most sensitive are frequently inhibited by the agitation that is necessary to keep insoluble salts suspended. The procedure described in Example I was repeated using Culture CJB, an oxygen sensitive strain of *Streptococcus cremoris* from Marschall Products Divisions of Miles Laboratories, Inc. The results of this study are set out in Table II.

TABLE II

| | CJB Subculture acid prod'n | | | | Activity[a] test | Cell Numbers | |
|---|---|---|---|---|---|---|---|
| | 0 hrs | | 16 hour | | (Developed | (cfu/ml at | |
| | TA[d] | pH | TA[d] | pH | acidity) | 16 hours) | Settling[b] |
| Control (8.25% w/w) w/agitation | 0.56 | 6.82 | 0.74 | 6.67 | 0.10 | $2.0 \times 10^7$ | −during incubation +during storage |
| Control (8.25% w/w) w/o agitation | 0.55 | 6.83 | 1.61 | 5.85 | 0.25 | $1.1 \times 10^9$ | + |
| Medium XG[c] (8.25% w/w) w/agitation | 0.56 | 6.81 | 0.85 | 6.48 | 0.13 | $4.0 \times 10^7$ | −(5 days) |
| Medium XG[c] (8.25% w/w) w/o agitation | 0.57 | 6.81 | 2.15 | 5.62 | 0.40 | $1.8 \times 10^9$ | −(5 days) |

[a] 6 hr-30° C. activity test in 11% nonfat dry milk steamed with TA readings at 0 hours and 6 hrs (developed acidity is the change in TA readings at 0 and 6 hrs) - inoculation rate was 0.5%.
[b] Settling: − = no settling in the indicated time + = severe settling
[c] XG = Xanthan gum
[d] TA = Titratable acidity as lactic acid Table II illustrates the distinct advantage to the use of a bulk starter medium containing a stabilizer as contemplated by the present invention for the propagation of oxygen sensitive cultures. In all cases, even with stabilizer present, agitation severely inhibited growth due to oxygen incorporation; whereas, the use of a medium containing stabilizer without agitation resulted in normal culture development. Since there are a number of commercial cultures that are sensitive to the oxygen levels which occur during normal agitation in many starter tanks, the present invention will enhance the utility of media containing insoluble salts.

EXAMPLE III

A dry bulk control starter medium (without Xanthan Gum) was prepared as described in Example I. The Control was rehydrated with water to 8.25% total solids and two samples of Medium XG (prepared as in Example I) to 8.25% and 15.25% total solids, respectively. One percent inoculation was made with the CJB culture which had been grown for 16 hours as described in Example I. The incubation was carried out at 22.8° C. for 16 hours with the results being reported in Table III.

TABLE III

| 1 - Control (8.25% w/w) w/agitation | Suspension maintained |
|---|---|
| 2 - Control (8.25% w/w) w/o agitation | Total separation in 10 min |
| 3 - Medium XG (8.25% w/w) w/o agitation | Suspension maintained for 5 days |
| 4 - Medium XG (15.25% w/w) w/o agitation | Suspension maintained for 24 hours |

The data set out in Table III show that the use of Xanthan Gum in the medium resulted in complete and sustained suspension of the particulate material regardless of the solids level. At the normal medium solids level (8.25% w/w) suspension was maintained for 5 days at refrigeration temperature of 4° C. At 15.25% (w/w) suspension was maintained for at least 24 hours at the temperature of 4° C.

EXAMPLE IV

A second medium containing insoluble salts was prepared with the following composition:

| Whey | 48.9% |
|---|---|
| Dextrose | 7.0% |
| NZ Amine | 2.86% |
| Yeast | 1.0% |
| Mono Ammonium Phosphate | 13.71% |
| Di Ammonium Phosphate | 15.0% |
| Sodium Hexametaphosphate | 1.5% |
| Magnesium Hydroxide | 10.0% |

To a portion of the above Control formulation was added Xanthan Gum so that the final composition was as follows:

| Whey | 48.07% |
|---|---|
| Dextrose | 6.17% |
| NZ Amine | 2.03% |
| Yeast | 0.17% |
| Mono Ammonium Phosphate | 12.88% |
| Di Ammonium Phosphate | 14.17% |
| SHMP | 0.67% |
| Magnesium Hydroxide | 9.17% |
| Xanthan Gum | 6.67% |

The Control growth medium and the growth medium with Xanthan Gum (Medium XG) were hydrated with water to 7.0% total solids, heated with agitation to 87.8° C. for 40 minutes and cooled to 22.8° C.

One percent inoculations were made with cultures CC7 and EV4 strains of *Streptococcus cremoris* and M24, a strain of *Streptococcus lactis* all from Marschall Products Division of Miles Laboratories, Inc. grown as described in Example I. Incubation was carried out at 22.8° C. for 16 hours with the Control samples being agitated and the samples with Xanthan Gum grown quiescently. An activity test was carried out by inoculating 0.5% (v/v) of the above 16 hour growth into steamed 11% (w/w) nonfat dry milk and incubating at 89° F. for 5 hours. The results are set out in Table IV.

TABLE IV

| Sample | Culture | Subculture TA | pH | Activity Test 5 hr. TA |
|---|---|---|---|---|
| Control w/ agitation | CC7 | 1.66 | 5.42 | 0.47 |
| Medium XG w/o agitation | CC7 | 1.79 | 5.48 | 0.47 |
| Control | EV4 | 0.97 | 5.99 | 0.43 |
| Medium XG | EV4 | 2.06 | 5.44 | 0.73 |
| Control | M24 | 0.55 | 6.92 | 0.24 |
| Medium XG | M24 | 1.64 | 5.58 | 0.59 |

From Table IV it can be determined that culture growth and performance in Medium XG were equal to or greater than the Control with agitation.

What is claimed is:

1. In combination with the method of propagating a mother culture of an acid producing bacteria which involves inoculating an aqueous bulk starter medium containing a nutrient base, a growth stimulant, a phage control agent and an essentially insoluble or temporarily insolubilized particulate neutralizing agent, the improvement which comprises incorporating into the starter medium before propagation of the mother culture a food-grade protective hydrocolloid as stabilizer in sufficient amount to prevent separation of the particulate neutralizing agent from the medium during such propagation of the mother culture in the absence of agitation.

2. The improvement of claim 1 wherein the neutralizing agent is magnesium phosphate, magnesium ammonium phosphate, calcium carbonate and magnesium hydroxide.

3. The improvement of claim 1 wherein the nutrient base is milk, why and dextrose, the growth stimulant is an enzyme hydrolyzed casein and/or yeast and the phage control agent is mono-ammonium phosphate, di-ammonium phosphate, sodium hexametaphosphate or a combination thereof.

4. The improvement of claim 3 wherein the neutralizing agent is magnesium phosphate or magnesium ammonium phosphate.

5. The improvement of claim 1 wherein the stabilizer is sodium carboxymethylcellulose, locust bean gum, sodium alginate, propylene glycol alginate, carrageenan and guar gum.

6. The improvement of claim 1 wherein the stabilizer is selected from the group of gum exudates, karaya, tragacanth and gum arabic.

7. The improvement of claim 1 wherein the stabilizer is xanthan gum.

8. The improvement of claim 1 wherein the amount of stabilizer is from 2% to 6% of the dry bulk starter medium on a weight basis.

9. In combination with the method of propagating a mother culture of an acid-producing bacteria which involves inoculating an aqueous bulk starter medium containing a nutrient base, a growth stimulant, a phage control agent and an essentially insoluble or insolubilized particulate neutralizing agent, the improvement which comprises incorporating into the starter medium xanthan gum in an amount of from 2% to 6% of the dry bulk starter medium on a weight basis.

10. The improvement of claim 9 wherein the neutralizing agent is magnesium phosphate or magnesium ammonium phosphate.

11. A dry blended bulk starter which comprises a nutrient base, a growth stimulant, a phage control agent and an essentially insoluble or insolubilized particulate neutralizing agent together with a foodgrade protective hydrocolloid as stabilizer in sufficient amount to prevent settling of the neutralizing agent when the bulk starter is placed in an aqueous medium and maintained in the absence of agitation.

12. The bulk starter of claim 11 wherein the neutralizing agent is magnesium phosphate or magnesium ammonium phosphate and the stabilizer is xanthan gum present in an amount of from 2% to 6% based on the combined dry weight of the nutrient base, growth stimulant, phage control agent and neutralizing agent.

13. The bulk starter of claim 11 wherein the particulate neutralizing agent has a particle diameter of 45 to 710 microns and is present in an amount of from 0.5 to 8 weight percent of the combined dry weight of the nutrient base, growth stimulant and phage control agent.

* * * * *